United States Patent
Banchereau et al.

(10) Patent No.: US 12,051,496 B2
(45) Date of Patent: Jul. 30, 2024

(54) METHODS AND APPARATUS FOR IDENTIFYING ALTERNATIVE SPLICING EVENTS

(71) Applicant: The Jackson Laboratory, Bar Harbor, ME (US)

(72) Inventors: Jacques Banchereau, Farmington, CT (US); Diogo Fernando Troggian Veiga, Farmington, CT (US); Anne Deslattes Mays, Farmington, CT (US)

(73) Assignee: The Jackson Laboratory, Bar Harbor, ME (US)

( * ) Notice: Subject to any disclaimer, the term of this patent is extended or adjusted under 35 U.S.C. 154(b) by 755 days.

(21) Appl. No.: 17/256,256

(22) PCT Filed: Jun. 26, 2019

(86) PCT No.: PCT/US2019/039150
§ 371 (c)(1),
(2) Date: Dec. 28, 2020

(87) PCT Pub. No.: WO2020/006028
PCT Pub. Date: Jan. 2, 2020

(65) Prior Publication Data
US 2021/0233640 A1    Jul. 29, 2021

Related U.S. Application Data

(60) Provisional application No. 62/692,325, filed on Jun. 29, 2018.

(51) Int. Cl.
*G16H 20/40*    (2018.01)

(52) U.S. Cl.
CPC ................... *G16H 20/40* (2018.01)

(58) Field of Classification Search
CPC .......... G16H 20/40; G16H 50/20; G06N 7/01; G16B 40/30; G16B 20/00
See application file for complete search history.

(56) References Cited

U.S. PATENT DOCUMENTS 10,865,229 B2 *  12/2020  Berglund ........... C07K 14/4702
10,870,885 B2 *  12/2020  Regev ................ G01N 33/5047
(Continued)

FOREIGN PATENT DOCUMENTS

CN    105483210 A  *  4/2016
CN    105483210 A     4/2016

OTHER PUBLICATIONS

Trincado et al "SUPPA2 fast, accurate, and uncertainty-aware differential splicing analysis across multiple conditions" (Year: 2018).*

(Continued)

*Primary Examiner* — Eliza A Lam
(74) *Attorney, Agent, or Firm* — Wolf, Greenfield & Sacks, P.C.

(57) ABSTRACT

Methods and apparatus for identifying alternative splicing events. The method comprises receiving a dataset of percent spliced in (PS I) values for each of a plurality of biological samples, wherein the plurality of biological samples includes a first population of samples having a first characteristic and a second population of samples having a second characteristic different from the first characteristic, fitting, to the dataset, a probabilistic model to identify clusters of samples in the dataset, calculating cluster characteristics for each of the clusters, filtering the clusters based, at least in part, on the cluster characteristics to identify a subset of clusters, each of which is associated with an alternative (Continued)

splicing event, and storing on the at least one storage device, information associated with the identified alternative splicing events.

21 Claims, 10 Drawing Sheets

(56) References Cited

U.S. PATENT DOCUMENTS

| | | |
|---|---|---|
| 2004/0048376 A1 | 3/2004 | Chabot et al. |
| 2012/0185178 A1* | 7/2012 | Williams ............... G16B 25/00 |
| | | 703/2 |
| 2017/0360873 A1* | 12/2017 | Blencowe ............ C12Q 1/6883 |
| 2021/0280875 A1* | 9/2021 | Ko ...................... H01M 8/2483 |

OTHER PUBLICATIONS

International Search Report and Written Opinion for International Application No. PCT/US2019/039150 mailed Sep. 26, 2019.
International Preliminary Report on Patentability for International Application No. PCT/US2019/039150 mailed Jan. 7, 2021.
Trincado et al., SUPPA2: Fast, Accurate, and Uncertainty-Aware Differential Splicing Analysis Across Multiple Conditions. Genome biology. Mar. 23, 2018;19(1):40.
Extended European Search Report for European Application No. 19826870.8, dated Mar. 7, 2022.
Barash et al., Model-based detection of alternative splicing signals. Bioinformatics. Jun. 15, 2010;26(12):i325-33.

\* cited by examiner

METHODS AND APPARATUS FOR IDENTIFYING ALTERNATIVE SPLICING EVENTS

CROSS-REFERENCE TO RELATED APPLICATIONS

This Application is a national stage filing under 35 U.S.C. § 371 of International Patent Application Serial No. PCT/US2019/039150, filed Jun. 26, 2019, which claims the benefit under 35 USC § 119(e) of U.S. Provisional Application Ser. No. 62/692,325, filed Jun. 29, 2018, entitled "METHODS AND APPARATUS FOR IDENTIFYING ALTERNATIVE SPLICING EVENTS". The contents of these applications are incorporated herein by reference in their entireties.

BACKGROUND

Despite progress in the development of effective targeted therapies and improved outcomes for many patients with diseases such as cancer, patients with some diseases or with treatment-resistant diseases continue to have an unmet medical need.

SUMMARY

Provided herein, in some aspects, is a molecular profiling platform that may be used, for example, to identify alternative splicing events that distinguish two populations of patients. Alternative splicing is a biological phenomenon that increases protein diversity. In alternative splicing, a part of the genetic code is either included within or excluded from messenger RNA (mRNA) produced from a gene. Consequently, proteins translated from the alternatively spliced mRNA will contain differences in their amino acid sequence, often resulting in differences in biological function. Therefore, alternative splicing events can produce distinct transcript isoforms. A common metric for evaluating the extent of alternative splicing events in a biological sample is percent spliced in (PSI or NJ), which represents the relative abundance of the splicing event in the sample.

The present disclosure provides, in some aspects, methods that combine the analysis (e.g., PSI values) determined for two populations of samples (e.g., normal and cancer tissue samples) and analyze the combined input using a probabilistic model to identify subpopulations of samples within the overall population that can be further analyzed to assess whether particular alternative splicing events are differentially expressed in the two populations of samples, even when the splicing event occurs in a subpopulation of the condition of interest. The samples may include any biological samples from which expressed alternative splicing events may be detected. For example, the biological samples may include, but are not limited to, fresh frozen tissues, cancer tissues, breast tissues, blood samples, urine samples, and cerebrospinal fluid (CSF) samples.

Any two populations of samples in which one or more splicing events are differentially expressed may be analyzed using the techniques described herein. For example, a first population of samples may be associated with patients having a particular disease (e.g., patients diagnosed with breast cancer), while a second population of samples may be associated with patients that do not have the particular disease (e.g., patients that have not been diagnosed with breast cancer). In another example, both populations may be associated with patients having a particular disease, with only one of the populations being associated with patients having a particular symptom or symptoms of the disease. In yet another example, a first population may include samples associated with patients having a disease from a category of diseases (e.g., patients having one or more of types of cancer), while a second population may include samples associated with patient that have not been identified as having a disease in the category of diseases. Other populations of samples may alternatively be analyzed using the techniques described herein, and embodiments are not limited in this respect.

Some embodiments are directed to a computer system for identifying alternative splicing events. The computer system comprises at least one computer processor and at least one storage device having stored thereon, a plurality of computer-readable instructions that, when executed by the at least one computer processor performs a method. The method comprises receiving a dataset of PSI values for each of a plurality of biological samples, wherein the plurality of biological samples includes a first population of samples having a first characteristic and a second population of samples having a second characteristic different from the first characteristic, fitting, to the dataset, a probabilistic model to identify clusters of samples in the dataset, calculating cluster characteristics for each of the clusters. filtering the clusters based, at least in part, on the cluster characteristics to identify a subset of clusters, each of which is associated with an alternative splicing event, and storing on the at least one storage device, information associated with the identified alternative splicing events.

Some embodiments are directed to a method of identifying cancer-specific alternative splicing events. The method comprises receiving a dataset of PSI values for each of a plurality of biological samples, wherein the plurality of biological samples includes a first population of samples having a first characteristic and a second population of samples having a second characteristic different from the first characteristic, fitting to the dataset, by at least one computer processor, a probabilistic model to identify clusters of samples in the dataset, calculating cluster characteristics for each of the clusters, filtering the clusters based, at least in part, on the cluster characteristics to identify a subset of clusters, each of which is associated with an alternative splicing events, and storing on at least one storage device, information associated with the identified alternative splicing events.

Some embodiments are directed to a non-transitory computer readable medium encoded with a plurality of instructions that, when executed by at least one computer processor perform a method. The method comprises receiving a dataset of PSI values for each of a plurality of biological samples, wherein the plurality of biological samples includes a first population of samples having a first characteristic and a second population of samples having a second characteristic different from the first characteristic, fitting to the dataset, a probabilistic model to identify clusters of samples in the dataset, calculating cluster characteristics for each of the clusters, filtering the clusters based, at least in part, on the cluster characteristics to identify a subset of clusters, each of which is associated with an alternative splicing events, and storing on at least one storage device, information associated with the identified alternative splicing events.

Some embodiments are directed to a method of treating a patient. The method comprises receiving a sample from the patient, assaying the sample to determine whether the sample includes one or more of a plurality of alternative splicing events included in an alternative splicing event panel, and providing a treatment to the patient based on whether the sample includes one or more of the alternative splicing events included in the panel, wherein the plurality of alternative splicing events included in the panel has been determined by fitting a probabilistic model to a dataset of PSI values for each of a plurality of biological samples to identify clusters of samples in the dataset, wherein the plurality of biological samples includes a first population of samples having a first characteristic and a second population of samples having a second characteristic different from the first characteristic, calculating cluster characteristics for each of the clusters, filtering the clusters based, at least in part, on the cluster characteristics to identify a subset of clusters, each of which is associated with an alternative splicing event in the alternative splicing event panel.

It should be appreciated that all combinations of the foregoing concepts and additional concepts discussed in greater detail below (provided such concepts are not mutually inconsistent) are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

DETAILED DESCRIPTION

Provided herein, in some aspects, are techniques for identifying alternative splicing events by analyzing a dataset of PSI levels determined for a plurality of biological samples that includes samples from two populations having different characteristics. For example, a first population may include samples obtained from patients having cancer and a second population may include samples obtained from patients that have not been identified as having cancer. Some conventional techniques for analyzing cancer tissue samples analyze a group of normal samples (non-cancerous samples) and a group of cancer samples (samples known to be cancerous) to generate two distributions (normal and cancer). In such techniques, it is assumed that the samples within each distribution have similar biological properties and that samples across distributions have different biological properties, such that the non-overlapping parts of the two distributions may be analyzed to assess the differences between the two groups of samples. The inventors have recognized that the conventional "two-distribution" approach is not appropriate for identifying alternative splicing events at least because such events can occur for reasons other than having cancer (e.g., alternative splicing events can occur naturally for non-cancerous (normal) healthy patients).

To this end, some embodiments are directed to a technique that takes into consideration the heterogeneity of alternative splicing events in biological data by fitting a probabilistic model to a dataset that includes data for samples from two populations having different characteristics (e.g., samples associated with patients having and not having cancer, or subpopulations of samples within a group of samples for patients having cancer). Rather than making assumptions about the two groups of samples, the techniques described herein employ a statistical approach to discover clusters of samples (that may include samples obtained from both normal tissue and cancerous tissue) that are specific to the differential characteristic(s) between the two populations of analyzed samples.

Figure 1:
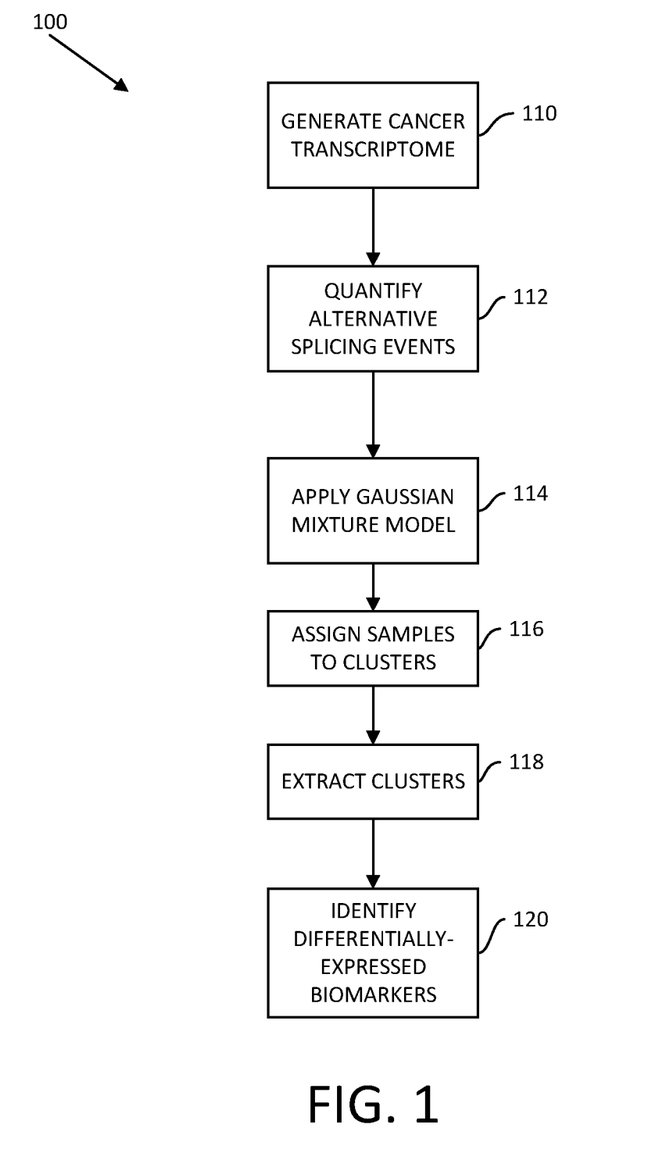
FIG. 1 illustrates a process for identifying alternative splicing events in accordance with some embodiments.

FIG. 1 illustrates a process 100 for identifying alternative splicing events in accordance with some embodiments. In act 110, a "cancer transcriptome" is generated. As noted above, in applications of technology described herein in which populations of biological samples other than samples with cancer are used, a transcriptome other than a cancer transcriptome may be generated in act 110. In one implementation, long read sequencing of samples having cancer was performed using Pacbio® Single Molecule Real Time Sequencing (SMRT) technology (see, e.g., Rhoads A et al. *Genomics Proteomics Bioinformatics* 2015; 13: 278-289, and Huddleston J et al. *Genome Research* 2014; 24: 688-696). This technology is capable of sequencing full-length cDNA transcripts without the need of cDNA fragmentation, and therefore can be used to directly infer the connectivity of exons in transcripts without the need for computational reconstruction. In particular, 81 biological samples in tissue cells lines with and without cancer were sequenced using the long read sequencing technology. Raw sequencing data was analyzed with ISO-Seq software provided by Pacbio. The output of the analysis (referred to herein as a "cancer transcriptome") was a non-redundant set of error-corrected isoform sequences aligned to the human genome build version hg38. Specifically, the output consisted of 298,000 distinct transcripts corresponding to ~14,000 genes, yielding a median of 8 isoforms per gene. This represented an approximately 2-fold increase over the human reference transcriptome (Gencode version 25) for those set of genes.

Process 100 then proceeds to act 112, where alternative splicing events in a dataset are quantified using the cancer transcriptome generated in act 110 as background. Several types of alternative splicing events have been discovered including, but not limited to, alternative 5' splicing exons, alternative 3' splicing exons, exon skipping, intron retention, and mutually exclusive exons. Beyond these basic types, more complex alternative splicing patterns are also possible. The examples described herein refer to quantifying and analyzing the extent to which exons are included in the mRNA produced by genes rather than being spliced out of the transcript via the alternative splicing event called "exon skipping." However, it should be appreciated that the techniques described herein may additionally or alternatively be used to identify and characterize any alternative splicing events differentially expressed in two populations of samples.

In some embodiments, RNA sequencing (RNA-seq) data is analyzed to determine read counts supporting different splicing events in the data. The relative abundance of a splicing event in the RNA-seq data may be quantified by a metric called percent spliced-in (PSI), as discussed briefly above. PSI values range from 0 to 1 (proportion scale) or 0% to 100% (percent scale). PSI values are calculated for exons undergoing alternative splicing, such as skipped exons or modified exons due to alternative 3' and 5' boundaries. PSI can also be computed for introns in order to evaluate intron retention. A formula for PSI may be given by:

$$\Psi = \frac{(I/l_1)}{(I/l_1 + S/l_s)},$$

where I is the number of read counts supporting the inclusion of an alternatively spliced exon/intron, S is the number of read counts supporting the skipping of the alternatively spliced exon/intron, $l_1$ is the length in base pairs of the inclusion region (harboring the exon/intron), and $l_s$ is the length in base pairs of the skipping region (removing the exon/intron). Accordingly, PSI quantifies the relative abundance of the inclusion form (I) over the total expression (I+S). Length normalization accounts for varying lengths of splice junctions.

In one implementation, exon skipping events were quantified from The Cancer Genome Atlas (TCGA) dataset, which is a publically-available dataset of genomic changes in 19 different types of cancer. It should be appreciated that datasets other than the TCGA dataset may alternatively be used in act 112. Quantifying alternative splicing events in act 112 may be performed by computing PSI values for portions of the genetic code (e.g., exons, introns, etc.) that undergo alternative splicing at splice junctions.

In one implementation, exon skipping events are quantified using rMATS (see e.g., Shen et al. *Proceedings of the National Academy of Sciences* 2014; 111(51):E5593-601). RNA-Seq data of cancer patients and the cancer transcriptome sequenced using SMRT Pacbio, as described above in connection with act 110 were provided as input to rMATS. 67,255 exon skipping events were identified in the cancer transcriptome, and the PSI values for each of those exons was computed across all samples (n=9,366). Each sample was processed separately with rMATS, and the results were combined in the a so-called "PSI matrix" of PSI levels which consisted of 67,255 rows, each of which corresponded to one of the identified exon skipping events and 9,366 columns, each of which corresponded to an analyzed sample. As described above, each of the values in the PSI matrix is a value between 0 and 1 that represents the PSI for a particular sample (column) and a particular splicing event (row). It should be appreciated that the PSI matrix may have any suitable number of rows and columns, and embodiments are not limited in this respect. Additionally, in some embodiments, the PSI matrix may include data corresponding to multiple different types of alternative splicing events.

When exon skipping is the alternative splicing event considered, an exon $e_1$ can be spliced-in or spliced-out of mRNA produced by a gene. To calculate PSI, I corresponds to the number of read counts aligning to splice junctions supporting the inclusion of the alternatively spliced exon $e_1$ plus read counts aligning to the $e_1$ exon body, and S corresponds to the number of read counts aligning to the upstream-downstream junctions (i.e., reads were the exon $e_1$ is skipped).

Process 100 then proceeds to act 114, where a probabilistic model (e.g., a Gaussian Mixture Model (GMM)) is fit to the data in the PSI matrix. In some embodiments, a plurality of GMMs are fit to the data in one or more rows of the PSI matrix, where each of the GMMs includes a different number of Gaussian distributions that are used to explain the data. Any suitable number of Gaussian distributions may be used in the GMM. As an example, in one implementation, four GMMs ranging from one to four Gaussian distributions are fit to each row of the PSI matrix, and the GMM with the best fit to the data according to one or more criteria (e.g., the Bayesian information criterion) is selected for that row of the matrix.

Figure 3:
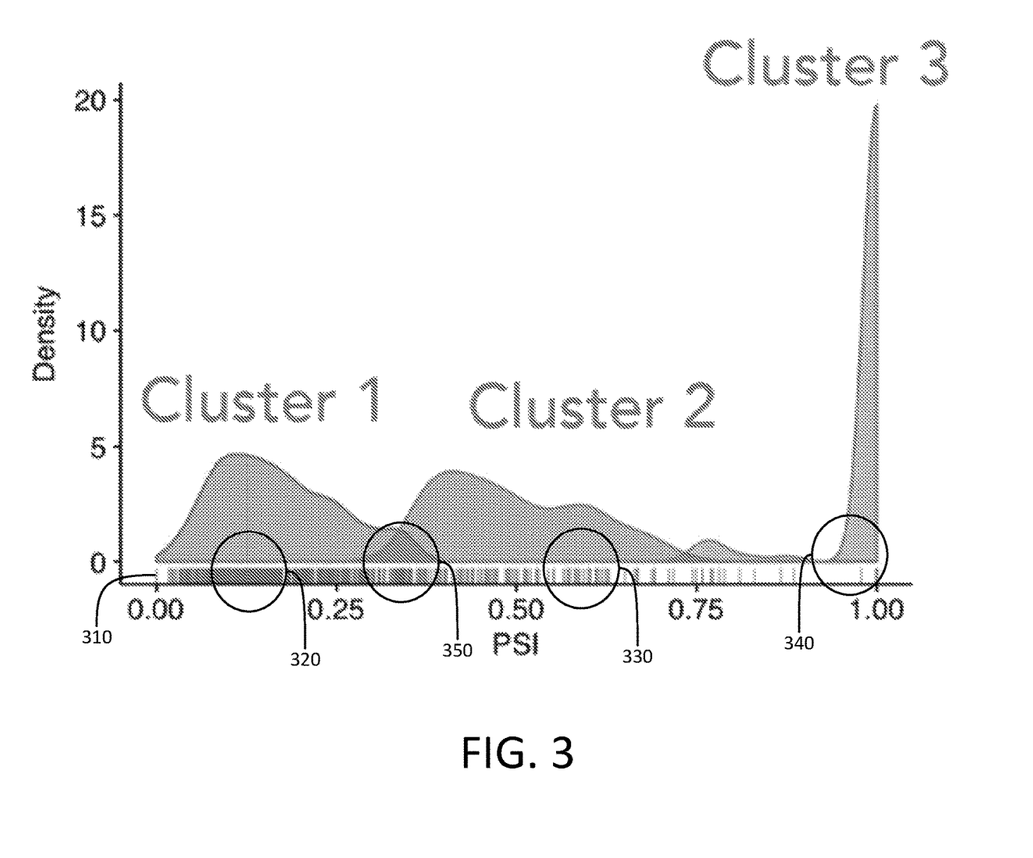
FIG. 3 schematically illustrates fitting a probabilistic model to PSI data to identify clusters in accordance with some embodiments.

FIG. 3 shows an example of a GMM with three Gaussian distributions fit to the data in a row of a PSI matrix using the techniques described herein. As shown, each of three Gaussian distributions in the GMM defines a subpopulation (cluster) of samples within the row of the PSI matrix. Represented along the PSI axis of the plot in FIG. 3 are the individual samples 310 within the row of the PSI matrix to which the Gaussian distributions were fit.

Accordingly, fitting a plurality of GMMs having different numbers of Gaussian distributions to the rows of the PSI matrix in this manner enables a determination of an optimal number of Gaussian distributions that accurately describes the heterogeneity of PSI levels within each row. In one implementation, fitting of the GMMs was performed using a plurality of computer-readable instructions programmed using the R computer language. In particular, the R package mclust (see Scurcca et al., *The R Journal* 2016; 8(1): 289-317) was used to perform Gaussian fitting and cluster analysis, described in more detail below. It should be appreciated that other computer languages, packages, or techniques may alternatively be used. In some embodiments, fitting of GMMs to rows of the PSI matrix is performed using a parallel function to allow multithreading analysis of the PSI matrix.

Although the example described above fits GMMs to single rows of the PSI matrix, in some embodiments, probabilistic models (e.g., GMMs) may be fit to data in more than one row of the PSI matrix to generate, for example, multi-dimensional (e.g., two-dimensional) distributions. Fitting GMMs across multiple rows may uncover subpopulations of samples corresponding to interactions between different splicing events represented by the different rows of the matrix.

Process 100 then proceeds to act 116, where samples are assigned to each of the clusters for a row (or multiple rows). As shown in FIG. 3, for some samples 310, assignment of samples to a particular cluster is straightforward. For example, samples in region 320 are assigned to cluster 1, samples in region 330 are assigned to cluster 2, and samples in region 340 are assigned to cluster 3. However, some samples are located within an overlap region (e.g., region 350) of multiple distributions corresponding to different clusters (in the case of region 350, cluster 1 and cluster 2). Based on its location along the PSI axis and the overlapping distributions, each of the samples may be associated with a probability that the sample belongs to each of the multiple overlapping clusters. For example, sample A may have a probability of 0.6 that it belongs to cluster 1 and a probability of 0.4 that it belongs to cluster 2. To ensure that each sample is only assigned to one cluster, the sample may be assigned based on which cluster is associated with the highest probability (e.g., sample A would be assigned to cluster 1 in the example above). Other metrics may additionally or alternatively be used for assigning samples in overlapping regions to clusters.

Process 100 then proceeds to act 118 where clusters are extracted from the dataset to which a GMM has been fit to data in the PSI matrix. As discussed above, in some embodiments, a plurality of GMMs having different numbers of Gaussian distributions are fit to each row of the data in the PSI matrix and one of the plurality of GMMs that provides a best fit to the data in the row is selected to represent the data in that row. Each of the Gaussian distributions in the selected GMM for a row defines a cluster of samples for the row (with each column of the matrix representing a different sample), and samples are assigned to the clusters as discussed above. After the samples are assigned to each cluster, one or more characteristics of the clusters are calculated in act 118, and the cluster characteristics are used to determine which clusters should be included in the panel of biomarkers for alternative splicing events that characterize a difference between the two populations of samples under study. Illustrative techniques for calculating cluster characteristics in accordance with some embodiments are described below in connection with FIG. 2. Process 100 then proceeds to act 120, where a panel of alternative splicing events are identified based on the extracted clusters.

Figure 2:
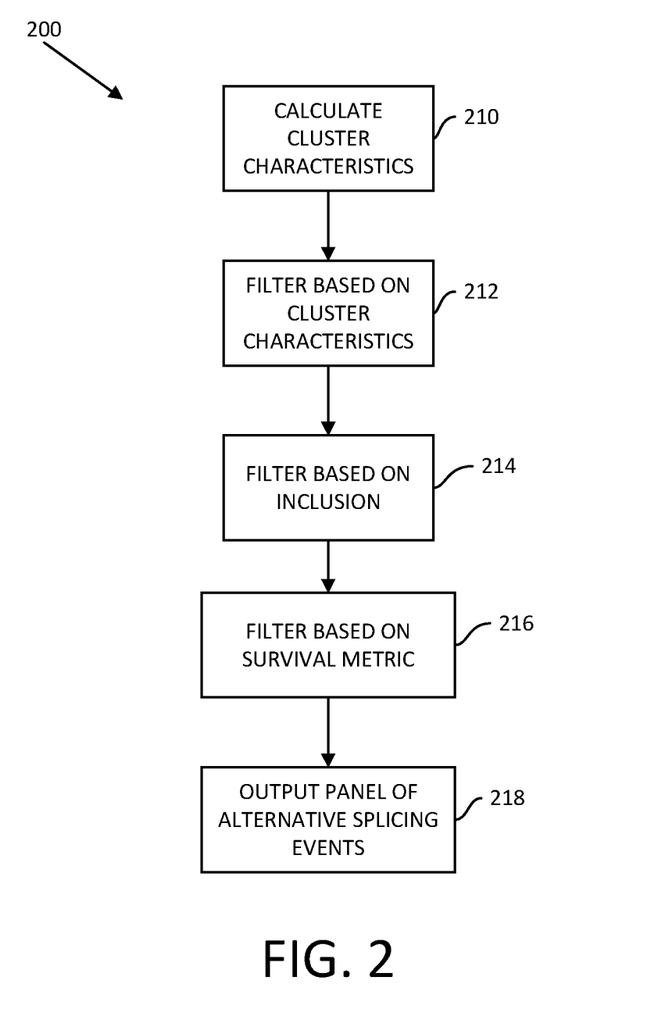
FIG. 2 illustrates a process for analyzing data clusters in accordance with some embodiments.

FIG. 2 illustrates a process 200 for performing filtering of clusters extracted from a dataset fit with GMMs as discussed above to determine a panel of alternative splicing events (e.g., exon inclusion events) that represent biomarkers for a particular differential characteristic or disease between two populations of samples (e.g., cancerous tissue and non-cancerous tissue). In act 210, at least one cluster characteristic is calculated for each of the clusters that form subpopulations of data in the PSI matrix. For example, if a particular row includes three clusters, at least one cluster characteristic may be calculated for each of the three clusters. Any suitable cluster characteristic(s) may be calculated to be able to select splicing events of interest across the two populations of samples. In one example, a differential splicing characteristic for a cluster may be calculated to determine the difference in relative abundances (e.g., $\Delta\Psi$) between the samples in the two populations. For example, differential splicing may be determined as:

$$\Delta\Psi = |\Psi_1 - \Psi_2| \geq c,$$

where c defines a threshold value (e.g., 0.1 or 0.2). Another example of a cluster characteristic that may be calculated in accordance with some embodiments is purity of the cluster. Purity of the cluster represents a percentage of the samples in the cluster that have a characteristic of interest divided by the total number of samples in the cluster. For example, when 90% of the samples in the cluster are associated with an alternative splicing event of interest, the purity of the cluster may be considered to be 90%. Other cluster characteristics may include, but are not limited to, the number of samples of interest in the cluster, very low or absent expression of the splicing event expression in one of the sample populations (e.g., expression in normal tissues), and survival information associated with patients from whom the samples in the cluster were obtained.

Figure 4:
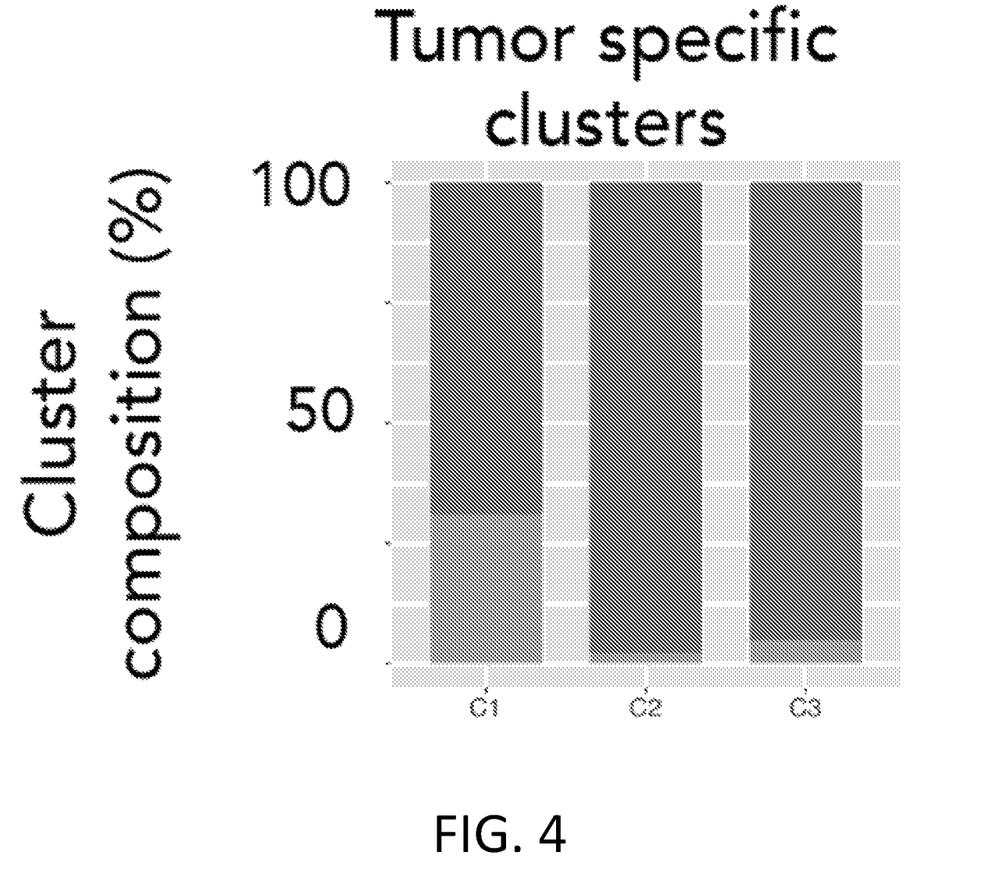
FIG. 4 illustrates a plot of cluster characteristics determined for identified clusters in accordance with some embodiments.
Figure 5:
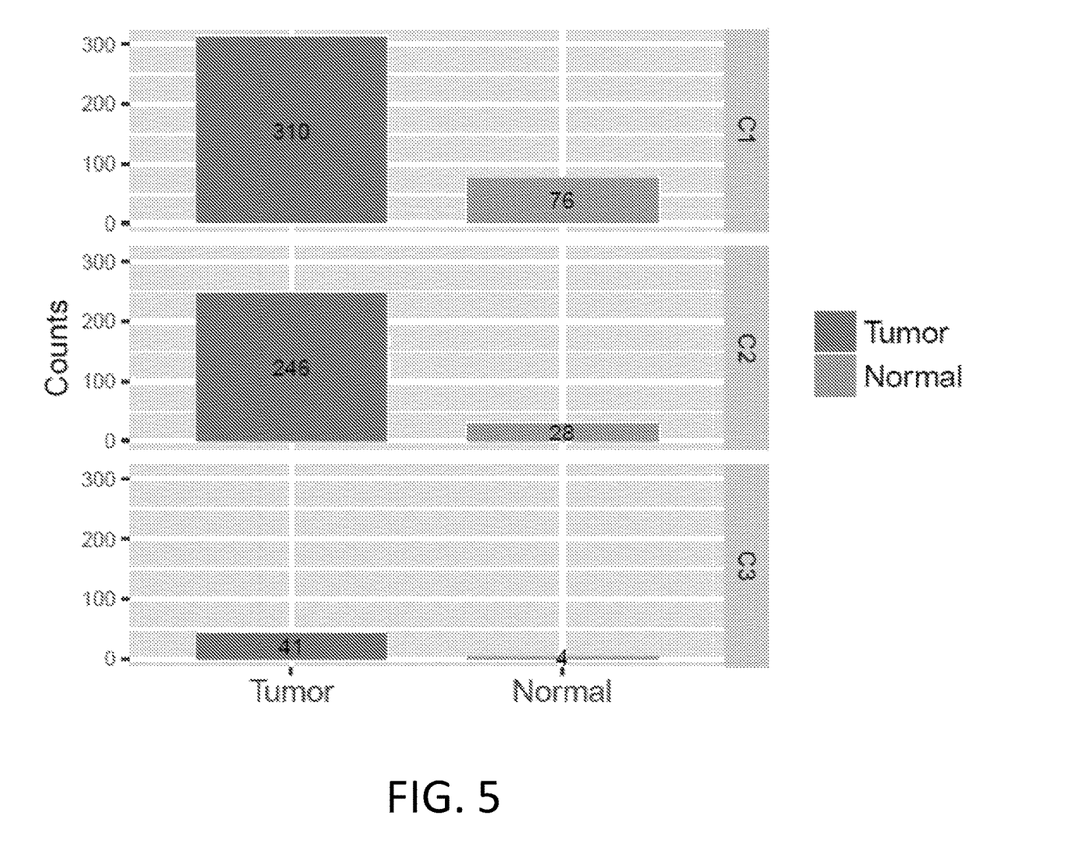
FIG. 5 illustrates another plot of cluster characteristics determined for identified clusters in accordance with some embodiments.
Figure 6:
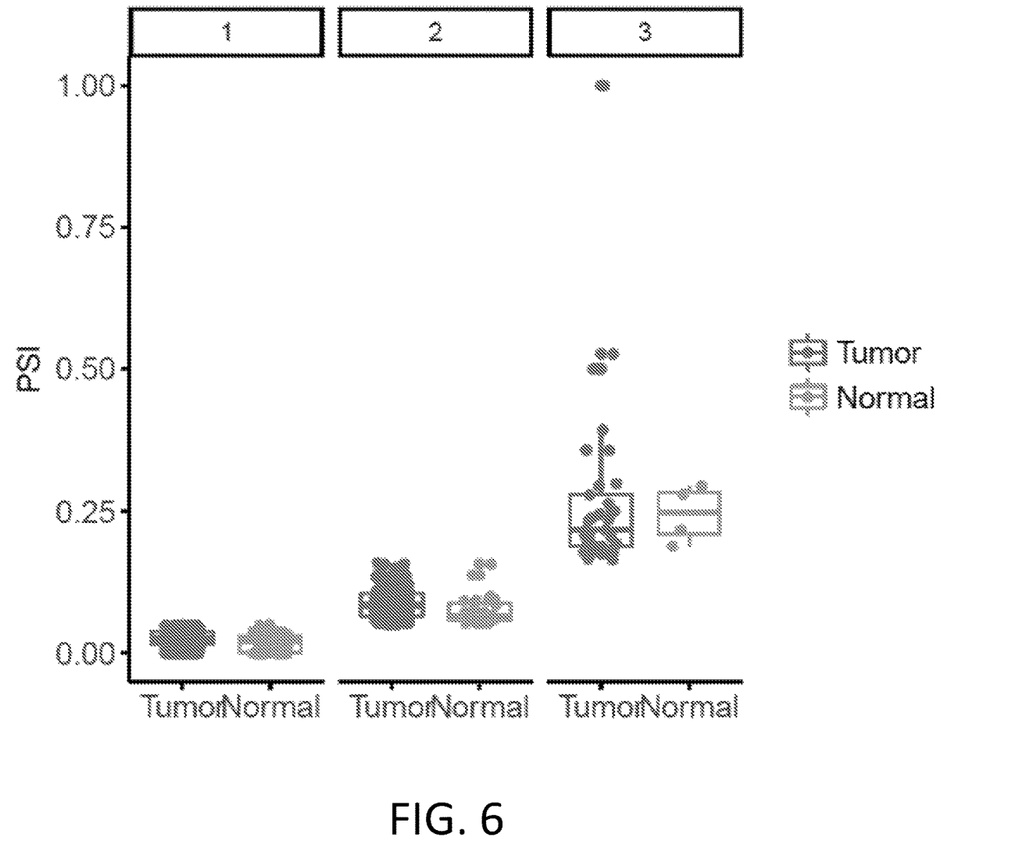
FIG. 6 illustrates a scatterplot showing cluster characteristics determined for identified clusters in accordance with some embodiments.
Figure 7:
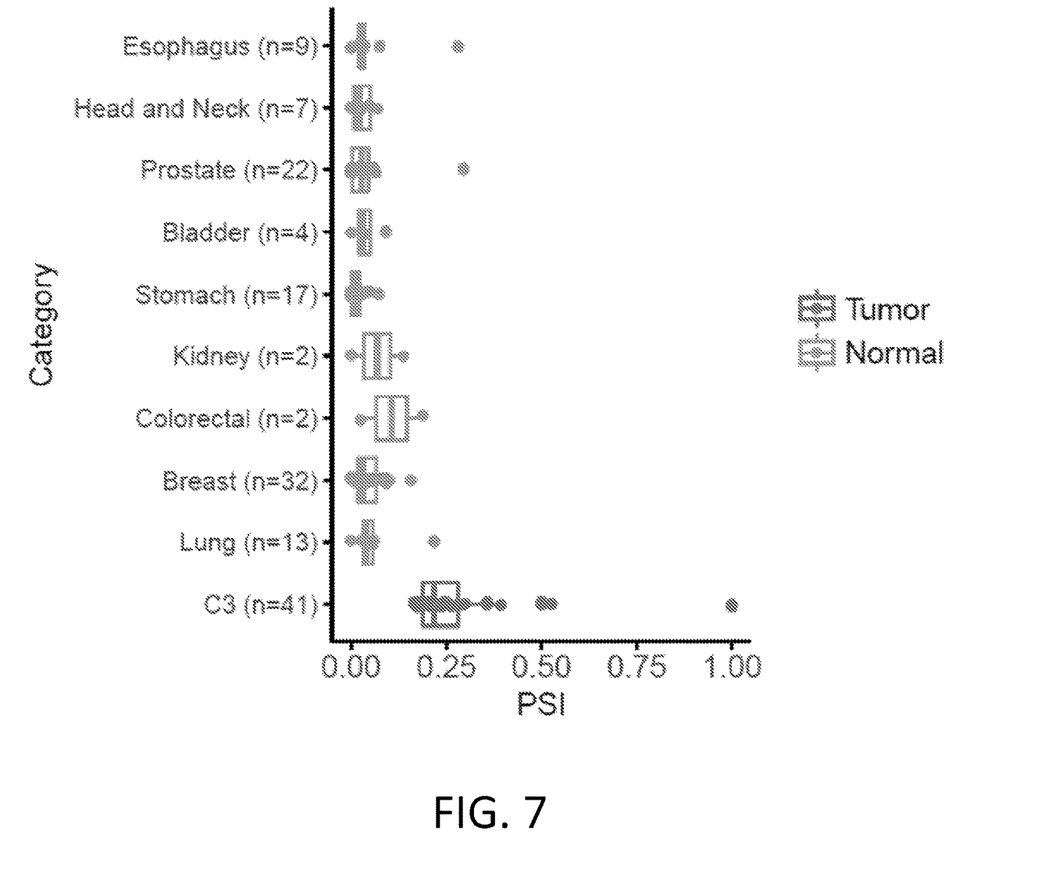
FIG. 7 illustrates a plot of cluster characteristics for a particular identified cluster compared to normal data in accordance with some embodiments.
Figure 8:
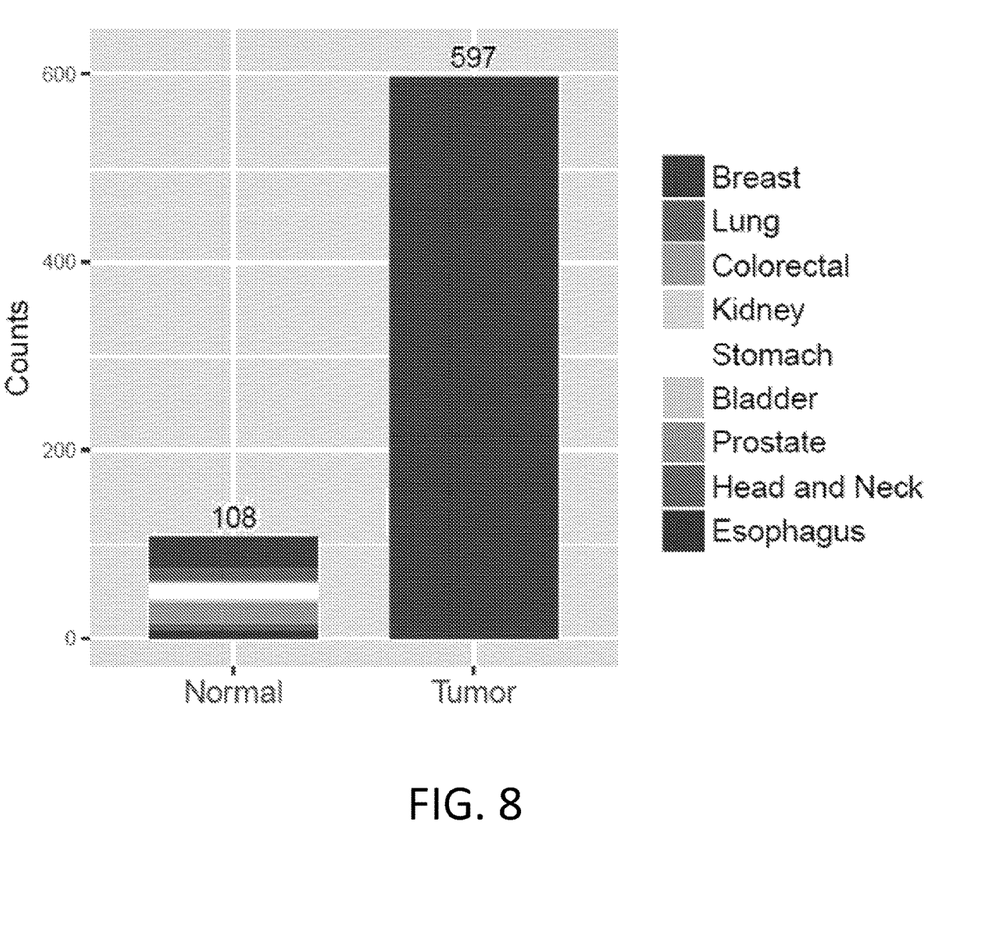
FIG. 8 illustrates a plot of the number of samples (with and without cancer) included in the probabilistic modelling analysis in accordance with some embodiments.

In one implementation in which the two populations are samples with and without cancer, a proportion of samples having cancer (or alternatively a proportion of samples without cancer) within each cluster may be determined. FIG. 4 illustrates a plot of cluster composition in which a proportion of samples in the cluster having cancer and without cancer for each of three clusters is shown. FIG. 5 shows a plot of the numerical counts of each sample type (e.g., cancer, normal) within each of the clusters C1, C2, and C3 of a row of the PSI matrix. For example, cluster C3 includes 41 samples having cancer and 4 samples without cancer. FIG. 6 shows PSI values for each of three clusters C1, C2, and C3 grouped by samples having cancer and samples without cancer. FIG. 7 shows a comparison between PSI values for a cluster C3 associated with cancerous tissues and PSI values for all normal tissues in the TCGA dataset. FIG. 8 shows a total number of samples (e.g., cancerous and normal) used in a GMM analysis in accordance with one implementation of the techniques described herein. In this example, samples from 597 breast cancer patients and 108 normal tissue samples were used in the GMM analysis. One or more of the aforementioned cluster characteristics and/or any other suitable cluster characteristics may be calculated in act 210, and embodiments are not limited in this respect.

Process 200 then proceeds to act 212, where the clusters identified in the PSI matrix are filtered based, at least in part, on the cluster characteristics identified in act 210. For example, one or more inclusion criteria for including a cluster in a subset of clusters may be specified, and the cluster characteristics may be used to determine whether a particular cluster meets the inclusion criteria. Clusters with increased expression in samples with cancer may be identified using one or more of the following cluster characteristics: cluster includes greater than a threshold percentage (e.g., 90%) of samples with cancer (i.e., purity of the cluster is >90%); cluster includes greater than threshold percentage increase in PSI values compared to normal (e.g., $\Delta\Psi > 10\%$, where $\Delta\Psi = \Psi_{cancer} - \Psi_{normal}$); and cluster has greater than a threshold number of samples (e.g., 30 samples with cancer). In some embodiments, clusters with decreased inclusion may also be identified using, for example, one or more of the following criteria: cluster includes greater than a threshold percentage (e.g., 90%) of samples with cancer; cluster includes greater than threshold percentage increase in PSI values compared to samples with cancer (e.g., $\Delta\Psi > 10\%$, where $\Delta\Psi = \Psi_{normal} - \Psi_{cancer}$); and cluster has greater than a threshold number of samples (e.g., 30 samples with cancer).

As described above, in some embodiments, the inclusion of clusters into the subset may further be restricted to require very low or absent expression of the alternative splicing event in one of the two populations of samples (e.g., tissues without cancer). For example, expression only (or mostly only, e.g., >95%) in samples with cancer may be required for inclusion into the subset of splicing event biomarkers.

Figure 9:
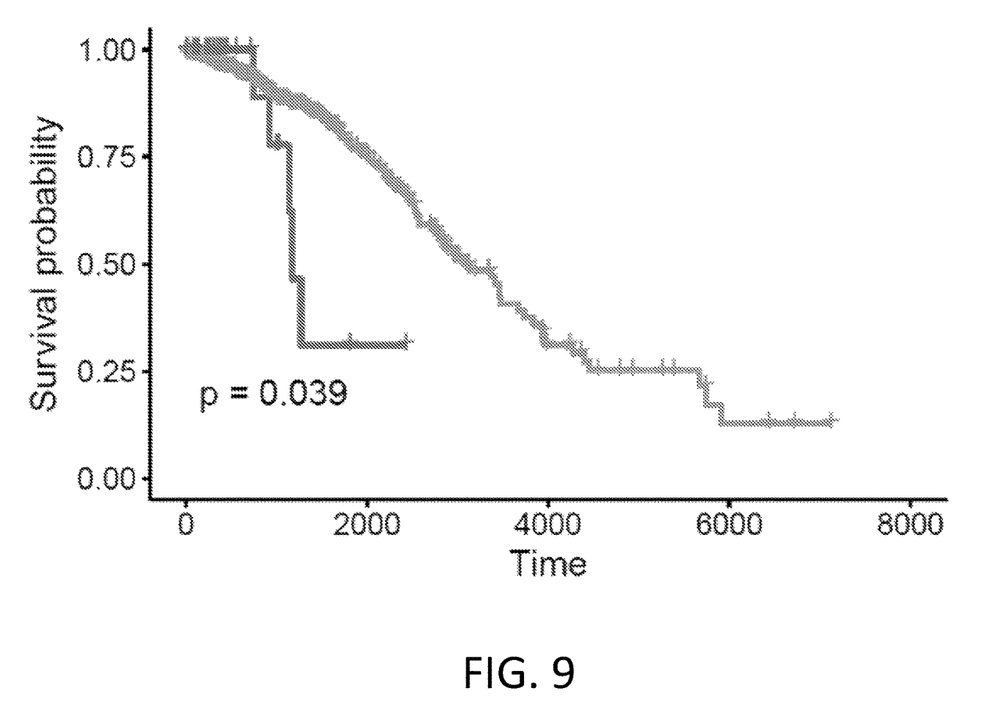
FIG. 9 illustrates a survival analysis plot for a particular identified cluster in accordance with some embodiments.

In some embodiments, the inclusion of clusters into the subset may further be determined based, at least in part, on survival information associated with the samples from which the data in the PSI matrix was determined. Survival information for patients from which the samples were obtained may be compared to survival information for other patients in the cohort. For example, FIG. 9 shows a survival analysis of patients in a cluster C3 versus the remaining patients in TCGA. This analysis indicates that patients in C3 (e.g., expressing an alternative exon) have worse overall survival (lower survival time, e.g., in days) than patients that are not in cluster C3.

Figure 10:
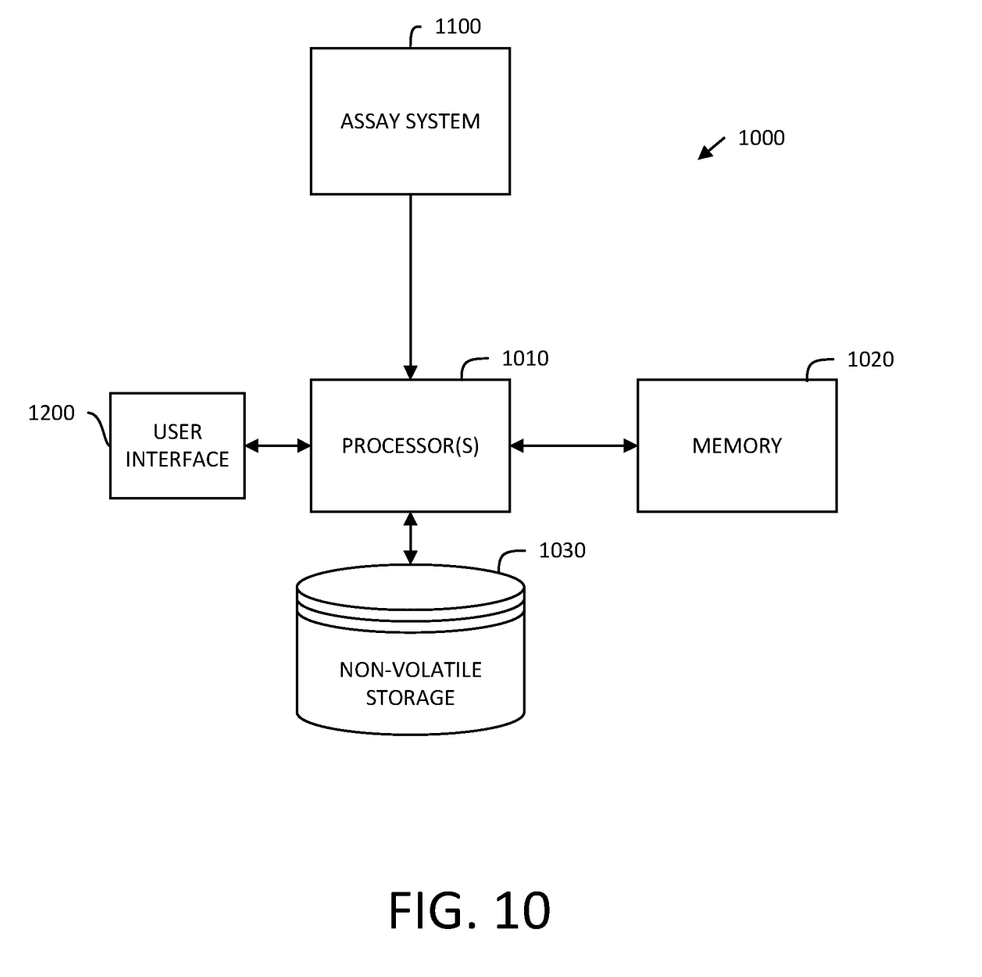
FIG. 10 schematically illustrates components of a computer-based system on which some embodiments may be implemented.

An illustrative implementation of a computer system 1000 that may be used in connection with any of the embodiments of the disclosure provided herein is shown in FIG. 10. The computer system 1000 includes one or more computer hardware processors 1010 and one or more articles of manufacture that comprise non-transitory computer-readable storage media (e.g., memory 1020 and one or more non-volatile storage devices 1030). The processor(s) 1010 may control writing data to and reading data from the memory 1020 and the non-volatile storage device(s) 1030 in any suitable manner. To perform any of the functionality described herein, the processor(s) 1010 may execute one or more processor-executable instructions stored in one or more non-transitory computer-readable storage media (e.g., the memory 1020), which may serve as non-transitory computer-readable storage media storing processor-executable instructions for execution by the processor(s) 1010.

In some embodiments, computer system 1000 also includes an assay system 1100 that provides information to processor(s) 1010. Assay system 1100 may be communicatively coupled to processor(s) 1010 using one or more wired or wireless communication networks. In some embodiments, processor(s) 1010 may be integrated with assay system in an integrated device. For example, processor(s) 1010 may be implemented on a chip arranged within a device that also includes assay system 1100.

Assay system 1100 may be configured to perform an assay on a biological sample from a patient to determine whether the sample includes one or more alternative splicing events included in an alternative splicing event panel. For example, if the panel includes twenty alternative splicing events (e.g., exon inclusion events), the assay system 1100 may be configured to determine whether the biological sample expresses any of the twenty alternative splicing events in the panel and that information may be provided to processor(s) 1010.

In some embodiments, computer system 1000 also includes a user interface 1200 in communication with processor(s) 1010. The user interface 1200 may be configured to provide a treatment recommendation to a healthcare professional based, at least in part, on the results of an assay provided by assay system 1100. In some embodiments, the treatment recommendation may additionally be based on survival information associated with one or more of the alternative splicing events in the panel, such that the treatment recommendation may be used to treat the patient in a more personalized or targeted manner than if the patient was treated merely based on symptoms, for example, observed by the healthcare professional.

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term). The phraseology and terminology used herein is for the purpose of description and should not be regarded as limiting. The use of "including," "comprising," "having," and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

The invention claimed is:

1. A computer system for identifying alternative splicing events, the computer system comprising:
   at least one computer processor; and
   at least one storage device having stored thereon, a plurality of computer-readable instructions that, when executed by the at least one computer processor performs a method comprising:
      receiving a dataset of percent spliced in (PSI) values for each of a plurality of biological samples, wherein:
         the dataset of PSI values comprises a matrix of rows and columns wherein each row of the matrix corresponds to a different alternative splicing event, and each column of the matrix corresponds to a different sample of the plurality of biological samples; and
         the plurality of biological samples includes a first population of samples having a first characteristic and a second population of samples having a second characteristic different from the first characteristic;
      fitting, to the dataset, a probabilistic model comprising a Gaussian Mixture Model to identify clusters of samples in the dataset, wherein fitting the probabilistic model comprising a Gaussian Mixture Model to the dataset comprises:
         fitting a plurality of Gaussian Mixture Models to each row of the matrix, wherein each of the plurality of Gaussian Mixture Models includes a different number of Gaussian distributions; and
         selecting, for each row of the matrix, one of the plurality of Gaussian Mixture Models having a best fit to data in the row, wherein selecting is based on a Bayesian information criterion;
      calculating cluster characteristics for each of the clusters;
      filtering the clusters based, at least in part, on the cluster characteristics to identify a subset of clusters, each of which is associated with an alternative splicing event; and
      storing on the at least one storage device, information associated with the identified alternative splicing event.

2. A computer system for identifying alternative splicing events, the computer system comprising:
   at least one computer processor; and
   at least one storage device having stored thereon, a plurality of computer-readable instructions that, when executed by the at least one computer processor performs a method comprising:
      receiving a dataset of percent spliced in (PSI) values for each of a plurality of biological samples, wherein:
         the dataset of PSI values comprises a matrix of rows and columns wherein each row of the matrix corresponds to a different alternative splicing event, and each column of the matrix corresponds to a different sample of the plurality of biological samples; and
         the plurality of biological samples includes a first population of samples having a first characteristic and a second population of samples having a second characteristic different from the first characteristic;
      fitting, to the dataset, a probabilistic model comprising a Gaussian Mixture Model to identify clusters of samples in the dataset, wherein fitting the probabilistic model comprising a Gaussian Mixture Model to the dataset comprises:
         fitting a plurality of Gaussian Mixture Models to the dataset, wherein each of the plurality of Gaussian Mixture Models is fit to two rows of the matrix, wherein each of the plurality Gaussian Mixture Models fit to a same two rows of the matrix includes a different number of Gaussian distributions; and
         selecting one of the plurality of Gaussian Mixture Models fit to the two rows of the matrix based on a best fit of the Gaussian Mixture Model to data in the two rows, wherein the selecting is based on a Bayesian information criterion;
      calculating cluster characteristics for each of the clusters;
      filtering the clusters based, at least in part, on the cluster characteristics to identify a subset of clusters, each of which is associated with an alternative splicing event; and
      storing on the at least one storage device, information associated with the identified alternative splicing event.

3. The computer system of claim 2, wherein calculating cluster characteristics for each of the clusters comprises determining a proportion of samples having the first characteristic in the cluster.

4. The computer system of claim 3, wherein filtering the clusters based, at least in part, on the cluster characteristics to identify a subset of clusters comprises selecting for inclusion in the subset, clusters in which greater than 90% of the samples in the cluster have the first characteristic.

5. The computer system of claim 4, wherein filtering the clusters based, at least in part, on the cluster characteristics to identify a subset of clusters comprises selecting for inclusion in the subset, clusters in which samples within the cluster having the first characteristic show a threshold increase in PSI values compared with samples within the cluster having the second characteristic.

6. The computer system of claim 5, wherein the threshold increase in PSI values is at least 10%.

7. The computer system of claim 6, wherein filtering the clusters based, at least in part, on the cluster characteristics to identify a subset of clusters comprises selecting for inclusion in the subset, clusters that include at least a threshold number of samples.

8. The computer system of claim 7, wherein the threshold number of samples is thirty samples.

9. The computer system of claim 8, wherein filtering the clusters based, at least in part, on the cluster characteristics to identify a subset of clusters comprises selecting for inclusion in the subset, clusters for which a proportion of samples within the cluster having the second characteristic is less than a threshold amount.

10. The computer system of claim 9, wherein the threshold amount is 5%.

11. The computer system of claim 8, wherein the method further comprises:
 receiving survival information associated with patients from which at least some of the plurality of samples were obtained; and
 filtering the clusters based, at least in part, on the survival information to identify the subset of clusters.

12. The computer system of claim 11, wherein filtering the clusters based, at least in part, on the survival information comprises selecting for inclusion in the subset, clusters for which patients associated with samples within the cluster having the first characteristic have a differential survival prognosis based on the survival information compared with patients associated with samples within the cluster having the second characteristic.

13. The computer system of claim 12, wherein the subset of clusters includes at least one first cluster associated with a worse survival prognosis for patients associated with samples having the first characteristic compared to patients associated with samples having the second characteristic and at least one second cluster associated with a better survival prognosis for patients associated with samples having the first characteristic compared to patients associated with samples having the second characteristic.

14. The computer system of claim 13, wherein the first characteristic comprises breast cancer.

15. The computer system of claim 14, wherein the first characteristic comprises a symptom of breast cancer.

16. The computer system of claim 15, further comprising:
 an assay system configured to assay a sample to determine whether the sample includes one or more of the alternative splicing events associated with the clusters in the subset.

17. The computer system of claim 16, wherein the method further comprises:
 providing a treatment recommendation when it is determined that the sample includes one or more of the alternative splicing events.

18. The computer system of claim 17, wherein providing a treatment recommendation comprises providing a treatment recommendation based, at least in part, on a survival prognosis associated with the one or more alternative splicing events included in the sample.

19. A method of identifying alternative splicing events, the method comprising:
 receiving a dataset of percent spliced in (PSI) values for each of a plurality of biological samples, wherein:
  the dataset of PSI values comprises a matrix of rows and columns, wherein each row of the matrix corresponds to a different alternative splicing event, and each column of the matrix corresponds to a different sample of the plurality of biological samples; and
  the plurality of biological samples includes a first population of samples having a first characteristic and a second population of samples having a second characteristic different from the first characteristic;
 fitting to the dataset, by at least one computer processor, a probabilistic model comprising a Gaussian Mixture Model to identify clusters of samples in the dataset, wherein fitting the probabilistic model comprising a Gaussian Mixture Model to the dataset comprises:
  fitting a plurality of Gaussian Mixture Models to each row of the matrix, wherein each of the plurality of Gaussian Mixture Models includes a different number of Gaussian distributions; and
  selecting, for each row of the matrix, one of the plurality of Gaussian Mixture Models having a best fit to data in the row, wherein the selecting is based on a Bayesian information criterion;
 calculating cluster characteristics for each of the clusters;
 filtering the clusters based, at least in part, on the cluster characteristics to identify a subset of clusters, each of which is associated with an alternative splicing event; and
 storing on at least one storage device, information associated with the identified alternative splicing events.

20. A non-transitory computer readable medium encoded with a plurality of instructions that, when executed by at least one computer processor perform a method, the method comprising:
 receiving a dataset of percent spliced in (PSI) values for each of a plurality of biological samples, wherein:
  the dataset of PSI values comprises a matrix of rows and columns, wherein each row of the matrix corresponds to a different alternative splicing event, and each column of the matrix corresponds to a different sample of the plurality of biological samples; and
  the plurality of biological samples includes a first population of samples having a first characteristic and a second population of samples having a second characteristic different from the first characteristic;
 fitting to the dataset, a probabilistic model comprising a Gaussian Mixture Model to identify clusters of samples in the dataset wherein fitting the probabilistic model comprising a Gaussian Mixture Model to the dataset comprises:
  fitting a plurality of Gaussian Mixture Models to each row of the matrix, wherein each of the plurality of Gaussian Mixture Models includes a different number of Gaussian distributions; and
  selecting, for each row of the matrix, one of the plurality of Gaussian Mixture Models having a best fit to data in the row, wherein the selecting is based on a Bayesian information criterion;
 calculating cluster characteristics for each of the clusters;
 filtering the clusters based, at least in part, on the cluster characteristics to identify a subset of clusters, each of which is associated with an alternative splicing event; and
 storing on at least one storage device, information associated with the identified alternative splicing events.

21. A method of treating a patient, the method comprising:
 receiving a sample from the patient;
 assaying the sample to determine whether the sample includes one or more of a plurality of alternative splicing events included in an alternative splicing event panel; and
 providing a treatment to the patient based on whether the sample includes one or more of the alternative splicing events included in the panel,
 wherein the plurality of alternative splicing events included in the panel has been determined by:
  fitting a probabilistic model comprising a Gaussian Mixture Model to a dataset of percent spliced in (PSI) values for each of a plurality of biological samples to identify clusters of samples in the dataset, wherein:
   the dataset of PSI values comprises a matrix of rows and columns, wherein each row of the matrix corresponds to a different alternative splicing event, and each column of the matrix corresponds to a different sample of the plurality of biological samples;

the plurality of biological samples includes a first population of samples having a first characteristic and a second population of samples having a second characteristic different from the first characteristic; and fitting the probabilistic model comprising a Gaussian Mixture Model to the dataset comprises:

fitting a plurality of Gaussian Mixture Models to each row of the matrix, wherein each of the plurality of Gaussian Mixture Models includes a different number of Gaussian distributions; and selecting, for each row of the matrix, one of the plurality of Gaussian Mixture Models having a best fit to data in the row, wherein the selecting is based on a Bayesian information criterion;

calculating cluster characteristics for each of the clusters; and filtering the clusters based, at least in part, on the cluster characteristics to identify a subset of clusters, each of which is associated with an alternative splicing event in the alternative splicing event panel.

* * * * *